United States Patent [19]

Sasamata et al.

[11] Patent Number: 5,102,787
[45] Date of Patent: Apr. 7, 1992

[54] METHOD, DEVICE AND KIT FOR MEASUREMENT OF TISSUE PLASMINOGEN ACTIVATOR ACTIVITY

[76] Inventors: Miho Sasamata, 678 Hiyoshihoncho, Kouhoku-ku, Yokohama-shi, Kanagawa, Japan, 223; Katsuhisa Ito, Shimogamo Higashi 723, Takano Tatehara-cho 1-3, Sakyo-ku, Kyoto-shi, Kyoto, Japan, 606; Masao Katoh, 5-48-9-102, Takashimadaira, Itabashi-ku, Tokyo, Japan, 175; Shinya Yano, 8-33-8, Takashimadaira, Itabashi-ku, Tokyo, Japan, 175; Eriko Matsumura, 873-3-501, Kamiochiai, Yono-shi, Saitama, Japan, 338; Hisanori Ezoe, 1-43-8, Uehara, Shibuya-ku, Tokyo, Japan, 151

[21] Appl. No.: 215,213

[22] Filed: Jul. 5, 1988

[30] Foreign Application Priority Data

Jul. 10, 1987 [JP] Japan ................................ 62-172300
Jul. 16, 1987 [JP] Japan ................................ 62-178073
Dec. 23, 1987 [JP] Japan ................................ 62-328004

[51] Int. Cl.$^5$ ................. G01N 33/543; G01N 33/577
[52] U.S. Cl. ..................................... 435/7.21; 435/7.4; 435/13; 435/23; 436/518; 436/548; 935/110
[58] Field of Search .................. 435/7, 13, 23, 810, 435/7.4, 975, 7.21; 436/518, 531, 810, 548; 530/387; 935/110

[56] References Cited

U.S. PATENT DOCUMENTS 4,629,694 12/1986 Harpel ..................................... 435/13
4,720,455 1/1988 Babu et al. .............................. 435/7
4,833,085 5/1989 Schaumann et al. ............. 435/172.2

FOREIGN PATENT DOCUMENTS 0032204 7/1981 European Pat. Off. .
0190711 8/1986 European Pat. Off. .
2095400 9/1982 United Kingdom .
2122219 1/1984 United Kingdom .

OTHER PUBLICATIONS

Norrman et al., Chem. Abstr., 108, 110510x, 1988.
Angles-Cano et al., Blood, 66, 913–920, 1985.
Holovet et al., Eur. Journ. Biochem., 158, 173–177, 1986.
Van Zonneveld et al., Thrombosis and Haemeostasis, 57, 82–86, 1987.

Primary Examiner—David Saunders

[57] ABSTRACT

A true activity of tissue plasminogen activator is determined by reacting a solid phase having bound thereto anti tissue plasminogen activator antibody IgG fraction having affinity to a site other than the active site of tissue plasminogen activator with tissue plasminogen activator in a sample and then measuring an activity of the reaction product, preferably in terms of an amount of a substance released from a chromogenic peptide substrate. This measurement enables to use of whole blood or diluted blood as the sample and achieves high sensitivity and high accuracy in a short period of time.

6 Claims, 12 Drawing Sheets

METHOD, DEVICE AND KIT FOR MEASUREMENT OF TISSUE PLASMINOGEN ACTIVATOR ACTIVITY

BACKGROUND OF THE INVENTION

1. Field of the Invention

The present invention relates to a novel method for measurement of the true activity of tissue plasminogen activator (hereafter referred to as t-PA) in blood and a device and kit as well as a novel monoclonal antibody used for the measurement. More particularly, the present invention relates to a method for measurement of the true activity of t-PA in blood which comprises using a solid phase having bound thereto anti t-PA-antibody IgG fraction having affinity to a site other than active site of t-PA and having specificity to t-PA in whole blood or diluted blood from which plasma is not separated as a sample, and measuring activator activity in the product of the solid phase and t-PA in the sample.

2. Description of the Prior Art t-PA is one of serine protease which takes part in fibrinolytic mechanism. It is known that its action is to prevent formation of thrombus by dissolving and removing fibrin formed in blood vessel or tissue. Further, t-PA is synthesized in blood endothelial cells and, secreted and released depending upon necessity and is thus a factor that is essential to prevention of thrombus formation and maintaining blood flow. From such, it is easily presumed that a high value of t-PA activity in blood would have a tendency to bleed and a low value would have a tendency to clot blood. However, so far no appropriate method has been developed yet, due to the presence of inhibitors(PAI) to t-PA in blood and to short half life of t-PA. In addition to those, t-PA can be readily inactivated under ice cooling even in plasma separated from blood. According to the results obtained in conventional methods for measurement, however, examples of clinical tests showing high t-PA levels are reported to be hepatic disorder [J. Clin. Invest., 43, 681 (1964), J. Clin. Pathol., 37, 772 (1983)], ovarian cancer [Eur. J. Cancer Clin. Oncol., 20, 577 (1984)], cerebral hemorrhage [Blood, 61, 267 (1983)]; regarding patients with low t-PA levels, there are reports on deep venous thrombus [Br. J. Surg., 70, 369 (1983), British Med. J., 290, 1453 (1985)], Atrophic Blanche [Arch. Pathol. Lab. Med., 110, 517 (1986)], endometrial malignant tumor [Cancer, 48, 1484 (1982)], myocardial infarction or hyperlipidemia [The New England Journal of Medicine, 313, No. 25, 1557 (1985)], etc. In addition, there is a report on the family line in which venous thrombus is repeated due to abnormality in t-PA production mechanism [Acta. Chim. Scand., 138, 313 (1972), Acta. Med. Scand., 203, 477 (1978)].

From the foregoing, it is also very important from the clinical aspect to know t-PA levels in blood.

In general, t-PA level in plasma has been hitherto determined by its amount of antigen and its activity. For determination of amount of antigen, RIA (radioimmunoassay), IRMA(immuno radiometric assay), ELISA (Enzyme linked-immunosorbent assay), etc. using anti t-PA antibody have been used (Published Unexamined Japanese Patent Application Laid Open Nos. 59-174759 and 61-148200).

On the other hand, the measurement of activity is roughly classified into two methods; namely, fibrinolysis and synthetic substrate method. For the fibrinolysis method, the following publications are given.
Thromb. Haemostas., 52 (1), 19 (1984)
Thromb. Haemostas., 45 (2), 107 (1981)
Thromb. Diathes. Haemoth., 32, 356 (1974)
For the synthetic substrate method, the following publications are given.
Thrombosis Res., 43, 129 (1986)
Thrombosis Haemostasis, 53 (3), 356 (1985)
Thrombosis Res., 46, 213 (1987)
Clinica. Chimica. Acta., 127, 279 (1983)

Further as materials for examining t-PA activity in blood, plasma is usually employed and for purposes of removing inhibitors to t-PA, various treatments are conducted. For example, there is a method which comprises centrifuging blood for 5 minutes, then separating plasma from the blood, immediately adjusting pH to 5.9 with acetic acid to precipitate Euglobulin fraction and centrifuging the precipitates [Thromb. Haemostas., 48 (3), 266 (1982)], a method which comprises adjusting pH of plasma to 3.9 and instantaneously freezing the plasma at $-70°$ C. (dry ice) (which is dissolved upon use with heating and its pH is readjusted to about 7.4) and a method which comprises adsorbing plasma t-PA to Lysine Sepharose and washing to remove t-PA inhibitor [Thrombosis Res., 46, 413 (1987)].

In each of the methods for determining the antigen level of t-PA, however, the reaction product of t-PA with its inhibitor is also measured as the amount of antigen but each method fails to measure true t-PA activity.

In addition, the conventional methods described above further involve serious problems in that:

(1) a time period necessary for centrifugation in order to separate plasma from blood takes at least 10 minutes from the start to the end of the operation, during which t-PA activity in plasma is greatly lost;

(2) it takes a long time until the result is judged (for about 20 hours ), which not only lacks simplicity but also fails to measure true t-PA activity, because t-PA inhibitor is continuously affecting the result during the reaction time, depending upon method; etc.

Furthermore, conventional methods require dilution from several ten to several thousand-fold thereby to avoid effects of t-PA inhibitor and thus encounter a problem that even t-PA activity cannot be measured, unless the methods are excellent in their sensitivity and accuracy.

From the foregoing reasons, all of the methods that can determine t-PA activity in blood as it is have not been successful.

Therefore, in order to establish a method for measurement of true t-PA activity, the present inventors have made extensive investigations on such a method for measuring t-PA activity in whole blood or diluted blood without centrifugation that inactivates the t-PA activity. As a result, they have found that true t-PA activity in a sample can be determined at high accuracy and sensitivity in an extremely simple treatment for a short time by the methods of either acting t-PA specific chromogenic peptide substrate directly on the reaction product obtained by reacting anti t-PA monoclonal antibody coupled with solid phase, or acting enzyme substrate specific to t-PA followed by reacting specific substrate to the plasmin produced by this reaction and, have come to reach the present invention.

SUMMARY OF THE INVENTION

Namely, the present invention is characterized by reacting, a solid phase having bound thereto anti t-PA antibody IgG fraction having affinity to a site other than the active site of t-PA with t-PA in whole blood or diluted blood and then determining accordingly an activity of the product, and an object of the present invention is to provide the method for determination.

Further, the present invention is characterized by containing at least a solid phase having bound thereto anti t-PA antibody IgG fraction having affinity to a site other than active site of t-PA and reagents for determining an activity of the reaction product between the IgG fraction bound to the solid phase and t-PA in whole blood or diluted blood. Another object of the present invention is to provide a kit for determination.

A further object of the present invention is to provide novel monoclonal antibody which is also used for the measurement method described above.

The present invention is also characterized by immobilizing a coated layer of anti t-PA-antibody IgG fraction having affinity to a site other than the active site of t-PA at one tip of a plastic stick and a still further object of the present invention is to provide such a measurement device.

DESCRIPTION OF THE PREFERRED EMBODIMENTS

Figure 1:
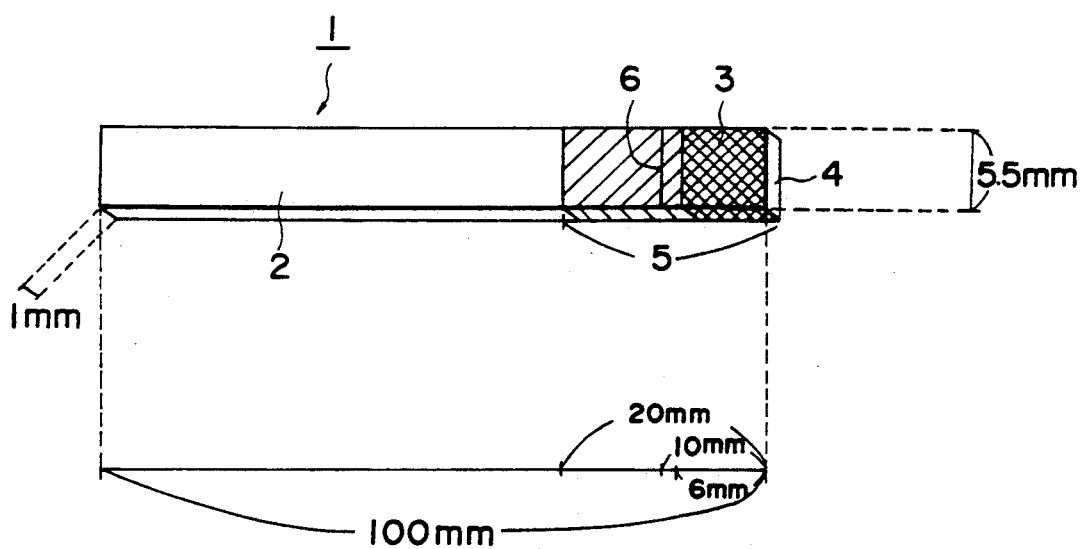
FIG. 1 is a perspective view of an anti-t-PA monoclonal antibody coated stick; wherein numeral 1 denotes a dipstick, numeral 2 denotes a stick, numeral 3 denotes an antibody coated area, numeral 4 denotes a tip, numeral 5 denotes BSA saturated area, and numeral 6 denotes a broken area.

Hereafter the present invention will be described in more detail.

Monoclonal antibody

The anti-t-PA monoclonal antibody of the present invention has specificity to t-PA and is specified in that its molecular weight is 153,000±10,000, IgG subclass is IgG 1, amino acid sequence of variable region in specific L-chain at the amino terminal end thereof is Asp-Ile-Val-Leu-Thr-Gln-Ser-Pro-Ala-Ser-Leu-Ala-Val-Ser and, an antigen binding site is at or near the fibrin-affinity site. In particular, the anti-t-PA monoclonal antibody having the aforesaid amino acid sequence is hitherto unknown and is a novel monoclonal antibody. The anti-t-PA monoclonal antibody includes any one that meets the conditions described above but an example is anti-t-PA monoclonal antibody SP-322 prepared by immunization of melanoma cell-derived t-PA. Monocolonal antibody SP-322 was deposited on Aug. 10, 1990, under Accession No. FERM BP-3052 in the Fermentation Research Institute, Agency of Industrial Science and Technology, Ministry of International Trade and Industry, located at 1-3, Higashi 1 chrome Tsukuba-shi, Ibaraki-ken 305, Japan, and a recognized international depository under the Budapest Treaty. Monoclonal antibody SP-322 is produced by mouse hybridoma SP-322 cells in culture orin mouse ascites. Mouse hybridoma clone SP-322 can be obtained by cell fusion BALB/C mouse spleen cells immunized by human melanoma cell-derived t-PA with mouse myeloma cells, for example, P3X63 Ag 8.U1 (P3U1) in a conventional manner, for example, cell fusion described by Köhler and Milstein (cf. examples later described).

As the medium for culturing the hybridoma cells described above, Delbecco's modified minimum essential medium (hereafter simply referred to as DMEM) can be used by supplementing with bovine fetal serum, L-glutamine, glucose, sodium pyruvate, 2-mercaptoethanol and antibiotics (for example, penicillin G, streptomycin, gentamycin, etc.), etc. In the present invention, hybridoma cell culture is generally performed either in the medium at 37° C. in the gaseous phase of 5% carbon dioxide and 95% air for 2 to 4 days or in the peritoneal cavity of BALB/C mouse pre-treated with 2,6,10,14-tetramethylpentadecane (Pristan, trademark, manufactured by Aldrich Co., Ltd.) for 10 to 20 days, whereby antibody can be produced in such an amount that can be purified.

The thus produced monoclonal antibody can be isolated and purified from the culture supernatant or ascitic fluids in a conventional manner used for isolation and purification of protein. Examples of such conventional manner include centrifugation, dialysis, salting out with ammonium sulfate, column chromatography using DEAE-cellulose, hydroxy apatite, protein A agarose, Sephadex (trademark, manufactured by Pharmacia Fine Chemicals Co., Ltd.), etc.

Method for measurement

The method for measurement of the present invention uses a solid phase having bound thereto anti-t-PA monoclonal antibody but is quite different from conventional ELISA using monoclonal antibody in that:

(1) enzyme antibody is not used; and,
(2) activity of t-PA is measured, not an amount of antigen.

In conventional ELISA, a part of sample t-PA binds to t-PA inhibitor under the condition of t-PA inhibitor is co-existed thereby to loose t-PA activity; in spite, the conjugated product of t-PA and t-PA inhibitor is also measured as an amount of t-PA antigen. The present invention is directed to a method for measurement of whole blood or diluted blood, in which inhibitor is also co-present, in a short period of time. In addition, the reaction product of t-PA and t-PA inhibitor is not the objective of the present measurement so that specifically true t-PA activity in blood can be determined.

The anti t-PA-antibody IgG fraction used in the present invention can be any anti-t-PA monoclonal antibody as long as it does not bind to the active site of t-PA but has specificity to t-PA. Thus, commercially available ESP-2 (t-PA monoclonal antibody manufactured by Bioscott Co., Ltd.,) and anti-t-PA monoclonal antibodies described in Published Unexamined Japanese Patent Application Laid Open Nos. 59-5121, 61-148200 and 61-181964 (or 61-183299) are all usable as far as they do not bind to the active site of t-PA. However, particularly preferred is anti-t-PA monoclonal antibody SP-322 described above since it is especially excellent in its affinity to t-PA.

As for the solid phase used in the present invention, any one capable of binding the aforesaid t-PA antibody can be used and there may be used, for example, microplates, beads, sticks, test tubes, etc. made of polymers such as polystyrene, polycarbonate, polypropylene, polyvinyl, etc. Of these, anti t-PA monoclonal antibody-bound stick which is excellent in simplicity upon use and will be later described is preferred.

The method for measurement of the present invention aims at treatment in a short period of time. Therefore, whole blood immediately after collecting blood from volunteers in the presence of anticoagulant is preferred as a test sample. As for the diluted blood specimen, blood obtained by diluting whole blood with dilution medium such as physiological saline, etc. to approximately 4 to 16-fold is preferred. In the method for measurement of the present invention, influence of t-PA inhibitor can be minimized by 4-fold dilution.

To determine the activity of the reaction mixture of the anti t-PA-antibody IgG fraction-bound solid phase and t-PA in a sample, chromogenic peptide substrate specific to t-PA is immediately added to the reaction product and an amount of a chromogenic or light-emitting substance released from the chromogenic peptide substrate is photometrically determined. Alternatively, enzyme substrate specific to t-PA is reacted with the reaction product in the presence or absence of stimulator, chromogenic peptide substrate specific to the plasmin reacted on the plasmin formed and, an amount of chromogenic or light-emitting substance released from the chromogenic peptide substrate is photometrically measured.

Herein, the chromogenic peptide substrate specific to t-PA can be any substrate as long as it reacts with t-PA and is decomposed to release chromogenic or light-emitting substance, whereby an amount of the chromogenic or light-emitting substance correlates to t-PA activity. Examples of such chromogenic peptide substrates that are commercially available include S-2288

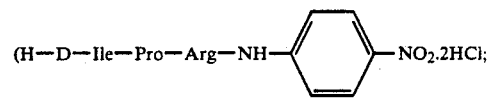

manufactured by Kabi Co., Ltd.), S-2444

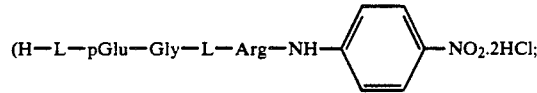

manufactured by Kabi Co., Ltd.),
etc. [cf. Published Unexamined Japanese Patent Application Laid Open No. 52-24581 (Published Examined Japanese Patent Application No. 56-15238), Public Disclosure No. 55-500076, etc.]. These substrates are all chromogenic and release p-nitroaniline. p-Nitroaniline has a characteristic absorption wavelength at 405 nm in visible yellow regions. In case that the chromogenic residues in the substrates described above are, for example, 4-methoxy-$\beta$-naphthylamide residue or 7-amino-4-methylcoumarine residue, they become fluorescent substrates though they are not commercially available. The released 4-methoxy-$\beta$-naphthylamine and 7-amino-4-methylcoumarine are excited by lights having exciting wavelengths of about 350 nm and about 380 nm, respectively and, their amounts can be determined by measuring fluorescence at about 420 nm and about 440 nm, respectively.

On the other hand, typical enzyme substrate specific to t-PA is plasminogen. Preferred examples are human lysine plasminogen, glutamyl plasminogen.

The stimulator which may be used for the measurement of the present invention can be any one as far as it stimulates enzyme activity of t-PA, is added to enhance sensitivity of the measurement system and has the property described above. Specific examples include cyanogen bromide-treated fibrinogen, soluble fibrinogen monomer, polylysine, fibrin, etc.

Enzyme produced upon the reaction of the product with t-PA specific substrate is plasmin when plasminogen is used as the enzyme substrate.

The chromogenic peptide substrate specific to the enzyme produced may be any enzyme as long as it reacts with t-PA and is decomposed to release a chromogenic or light-emitting substance, whereby an amount of the chromogenic or light-emitting substance correlates to activity of the enzyme produced and thus t-PA activity. In case the enzyme produced is, for example, plasmin, there can be exemplified those that can be substrate of plasmin in the substrates described in Published Unexamined Japanese Patent Application Laid Open No. 52-24581 (Published Examined Japanese Patent Application No. 56-15238) and Public Disclosure No. 55-500076 described above; or Published Unexamined Japanese Patent Application Laid Open No. 52-3494 (Published Examined Japanese Patent Application No. 56-22519), Published Unexamined Japanese Patent Application Laid Open No. 57-2253 (Published Examined Japanese Patent Application No. 62-57197), Published Unexamined Japanese Patent Application Laid Open No. 58-63399 (Published Examined Japanese Patent Application No. 61-9840), Published Unexamined Japanese Patent Application Laid Open Nos. 58-172354, 62-294695 and 62-294696, etc. Particularly preferably used are commercially available S-2251

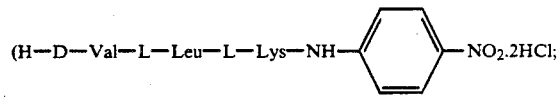

manufactured by Kabi Co., Ltd.), S-2302

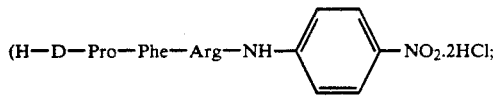

manufactured by Kabi Co., Ltd.),
Nr 51-32 (H-D-Val-SHT-Lys-pNa.2AcOH; manufactured by Pentapharm Co., Ltd.), Chromozym PL (Tos-Gly-Pro-Lys-pNA; manufactured by Boehringer Mannheim AG). In case that S-2251 or S-2302 is used as the chromogenic peptide substrate, p-nitroaniline is released as a chromogenic substance. Its measurement and fluorescent substrate are the same as described above.

Concretely, the measurement is conducted by:

(1) coating anti t-PA-antibody IgG fraction onto the solid phase, (2) washing the system to remove the unbound anti t-PA-antibody IgG fraction, (3) adding whole blood or diluted blood sample thereto to react with and bind to t-PA in the sample in a short period of time, (4) washing the system to remove the unbound components (whereby inhibitor is also removed), (5) adding chromogenic peptide substrate specific to t-PA, for example, S-2288 directly thereto to perform incubation; alternatively, adding further enzyme substrate specific to t-PA, for example, lysine plasminogen to step (4) and if the activity is too low, further adding thereto stimulator, for example, cyanogen bromide-treated fibrinogen and chromogenic peptide substrate specific to the enzyme produced e.g., plasmin, for example, S-2251, Nr. 51-32 or Chromozym PL to effect incubation, (6) measuring and quantitatively determining the released substance, and, (7) if necessary, calibrating it into t-PA activity.

Treatments such as washing, incubation, etc. are carried out using buffers having predetermined pH and ionic strength. Examples of such buffers include phosphate, carbonate, borate, citrate, barbiturate buffers, etc., Tris-HCl buffer, amino acid buffer, etc. While preference is somewhat different depending upon treatment, Tris-HCl buffer or Tris-HCl buffer supplemented with sodium chloride, Tween (polyoxyethylene sorbitan fatty acid ester) can be effectively used. As the reaction temperature, room temperature is sufficient for formation of the reaction product. In incubation for the measurement and quantitative determination, it is advantageous to conduct at about 37° C.

The quantitative determination using chromogenic peptide substrate is preferably conducted using conventional equipments such as a spectrophotometer, a fluorescence detector, etc., depending upon the nature of the released substance, after or without inactivating t-PA or enzyme produced.

Kit for measurement

The present invention includes the kit adapted to the measurement described above. The kit preferably includes all of the solid phase used for the determination method described above, anti-t-PA monoclonal antibody, reagent for t-PA activity measurement, i.e., t-PA-specific chromogenic peptide substrate, or enzyme substrate specific to t-PA and if necessary, stimulator, chromogenic peptide substrate specific to the enzyme produced and other standard solutions, in view of simplicity upon use but is not limited to the system in which all of these reagents are necessarily provided. Namely, the kit for measurement of the present invention is characterized by containing, at least, anti-t-PA monoclonal antibody or anti-t-PA monoclonal antibody bound to the solid phase and t-PA activity measurement reagent of the reaction product. The present invention includes all of the kit for t-PA activity measurement of whole blood or diluted blood containing them.

Device for measurement

Of the solid phase having bound thereto anti-t-PA monoclonal antibody, the present invention includes an anti-t-PA monoclonal antibody-bound stick which is excellent in simplicity upon use and most suited for treatment upon measurement in a short period of time.

Concretely, a dipstick for measurement of t-PA activity of the present invention is made of plastic and comprises an antibody coated area of anti t-PA-antibody IgG fraction having affinity to the site other than the active site of t-PA immobilized at one tip of the stick. Particularly preferred is a dipstick provided with a broken area that can be readily broken by bending at a well of a container used for the measurement as the support. Further, a measurement device comprising the stick previously contained in a vacutainer tube is also a preferred example of the present invention.

Hereafter the measurement device of the present invention will be described in detail with reference to the drawings showing examples.

Figure 2:
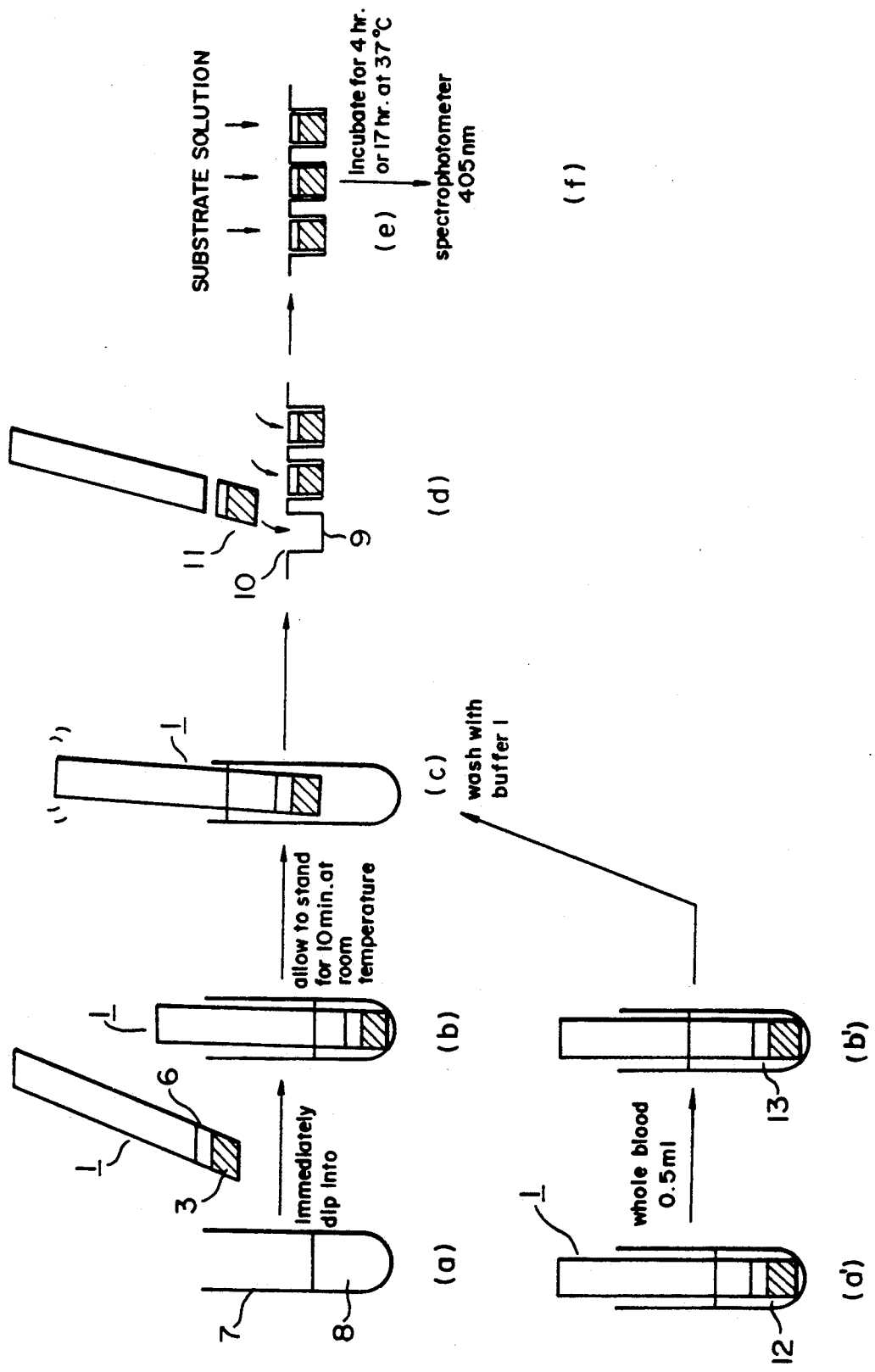
FIG. 2 is a flow chart showing a measurement method using a dipstick; wherein numeral 7 denotes a vacutainer tube, numeral 8 denotes whole blood, numeral 9 denotes microtiter plates, numeral 10 denotes a well, numeral 11 denotes a piece of dipstick, numeral 12 denotes Tris-HCl buffer, numeral 13 denotes diluted blood and numeral 14 denotes substrate solution.
- (a)→(b): Dipstick is immediately dipped into the vacutainer tube after blood collection.
- (b)→(c): The tube is allowed to stand for 10 minutes at room temperature.
- (a')→(b'): 0.5 ml of whole blood.
- (b')→(c): Washed with buffer I.
- (d)→(e): Substrate solution is added.
- (e)→(f): Incubation for 4 hours or 17 hours at 37° C. followed by measurement with a spectrophotometer at 405 nm.

FIG. 1 is a perspective view of a dipstick 1 of the present invention. FIG. 2 is a flow chart showing a method using the Dipstick 1.

Stick 2 is composed of a plastic material to which anti-t-PA monoclonal antibody can be bound and is of rectangular plate. As the plastic material, those exemplified for the solid phase are illustrated but particularly adequate are materials provided with a broken area that can be readily broken by bending at a well of a container used for the measurement as the support. A shape of the stick may be of any shape as long as it is of size capable of coating and immobilizing a predetermined amount of anti-t-PA monoclonal antibody and capable of operation by picking up the tip on the side, on which no anti-t-PA monoclonal antibody is coated, by fingers. A shape of the stick is not limited to the rectangular or plate shape shown in the drawing. In order to provide with a broken area that can be readily broken by bending at a well of a container used for the measurement as the support, however, the plate shown in the drawing is more preferred than the stick shape.

Anti-t-PA monoclonal antibody coated area 3 is provided at one tip of stick 2, where anti-t-PA monoclonal antibody is coated and immobilized. Coating and immobilization are carried out in a conventional manner. Namely, the stick is washed and dried. Then, the tip is dipped into a tube containing buffer. Coating is effected by allowing to stand for about 4 hours at room temperature; or allowing to stand overnight, when the temperature is at 4° C. The coated stick is put into a tube containing serum albumin, etc. Immobilization is performed by allowing to stand for about an hour at room temperature; or allowing to stand overnight, when the temperature is at 4° C. In the figure, numeral 5 denotes an area blocked with serum albumin. The area reaches 20 mm from the tip 4 of the stick in the figure but may be an area that can achieve the purpose of immobilization and can be more than the antibody coated area described above.

It is preferred that the coating should be made to completely dip the tip 4 of the stick into the upper surface of a substrate solution in the container (in the figure, to reach about 6 mm from the tip). The coating is made generally over the entire surface and back surface of the tip of stick 2 but may also be made on one surface.

The stick 2 is preferably provided with a broken area 6 previously. In the figure, it is preferred to provide a slit at the end where anti-t-PA monoclonal antibody is coated and immobilized or at the side toward the non-coating area and adjacent a well of a container (about 10 mm from the tip in the figure).

The broken area 6 is not limited to the slit illustrated in the figure but may be perforations or notches, etc. as long as it can be easily broken, in particular, can be easily broken by bending at a well of the container as the support.

A method for measurement using the dipstick 1 is explained by referring to FIG. 2 (1). Whole blood 8 is collected in a vacutainer tube 7 [(a), anticoagulant such as sodium citrate or heparin, etc. may also be contained in the vacutainer tube 7]. The dipstick 1 is dipped into the tube immediately after blood is collected. The system is allowed to stand for 5 to 120 minutes at room temperature to react with whole blood [(b)]. The dipstick 1 is withdrawn [(c)]. The dipstick 1 is inserted into a container 9 to which a substrate solution is to be added and broken by bending a well 10 as the support, whereby only the broken tip 11 including anti-t-PA monoclonal antibody coated area 3 is dropped into the container 9 [(d)]. A substrate solution is applied to the container 9 holding the broken tip 11 therein followed by incubation at 37° C. for approximately 30 minutes to 20 hours [(e)]. Then, the dipstick is withdrawn and subjected to a measurement device (not shown), where an amount of chromogenic or light-emitting substance released from the substrate is measured [(f)] (the reaction can be colorimetrically measured even after the reaction is stopped).

Further a method using diluted blood sample is explained by referring to FIG. 2 (2). Blood is collected in a vacutainer tube 7 containing dilution medium 12 and dipstick 1 and if necessary, anticoagulant [(a')]. The sample is immediately mixed and allowed to stand for 5 to 120 minutes at room temperature to react with diluted blood [(b')]. Then, the system is washed and treated as in (c) through (e) described above to make measurement.

The dipstick 1 can also be previously applied to the vacutainer tube 7 in the case of using whole blood, as in diluted blood 13. Namely, this is because the immobilized anti-t-PA monoclonal antibody is so stable as to withstand such a commercially available mode.

Further in diluted blood sample it is not impossible to adapt the method of application and mixing diluted medium immediately after blood collection without previously adding the diluted medium. However, the method shown in the figure is preferred because the present invention aims at treatment in a short period of time.

Effects of the Invention

The method for measurement of t-PA activity in accordance with the present invention makes measurement of true t-PA activity in blood for the first time and provides various advantages below in simplicity, sensitivity, accuracy, etc.

(1) Centrifugal operation is not required so that influence of t-PA inhibitor is reduced and possible inactivation of t-PA can be minimized.

(2) It is possible to determine t-PA activity within 100 to 130 minutes after blood collection, which is extremely shorter than in the conventional method (about 20 hours).

(3) It is possible to measure in plasma or diluted blood with a smaller dilution factor (approximately 4 to 16-fold ) than in conventional dilution (generally diluted to 50 to 3200-fold ) so that inactivation of t-PA can be prevented as small as possible thereby to make it possible to measure t-PA activity in higher sensitivity.

(4) It is unnecessary to adjust to an acidic state (pH 3.9) or freeze with dry ice ($-70°$ C.).

(5) Whole operation is extremely simple.

(6) In the system in which stimulator is incorporated, the sensitivity is highly enhanced.

Accordingly, the method for measurement of the present invention can be utilized not only for screening of t-PA, t-PA derivatives and other fibrinolytic accelerators or confirmation of clinical effects, etc. but also for diagnosis of specific diseases, monitoring of conditions and TDM (Therapeutic Drug Monitoring).

Further the kit for measurement of the present invention is advantageous in that the kit can be provided for simple measurement. In particular, the kit comprising anti t-PA-antibody IgG fraction-bound solid phase, especially the dipstick coated and saturated with anti t-PA-antibody IgG fraction and the kit comprising such a dipstick are extremely simply operated only by acting whole blood or diluted blood thereon, adding a reagent for measurement of the product to incubate and then measuring t-PA activity.

In addition, by using the dipstick, (1) there is no loss in activity with the dipstick having adsorbed thereto t-PA in blood followed by washing with buffer and the dipstick can be stored for a week (4° C.), which enables the measurement easy;

(2) monoclonal antibody is already immobilized so that washing is simple. For example, washing can be made directly with buffer retained in a beaker or with tap water;

(3) when stored at 4° C. in buffer, the coated and saturated dipstick is stable over a period of longer than 3 months; and, (4) the dipstick is also excellent in stability upon transportation.

The anti-t-PA monoclonal antibody SP-322 of the present invention obtained described above shows high affinity to t-PA and useful as an immunoabsorbant used to purify t-PA and derivatives thereof or as a reagent for determining an amount of antigen or activity of t-PA. It is assumed that the monoclonal antibody of the present invention would recognize kringle 2 domain of the t-PA molecule.

In order to use the monoclonal antibody of the present invention for purification of t-PA and derivatives thereof, anti-t-PA monoclonal antibody SP-322 is firstly reacted with activated agarose gel, for example, cyanogen bromide-activated Sepharose 4B (trademark, manufactured by Pharmacia Fine Chemicals Co., Ltd.) or Afigel 10 (trademark, manufactured by Biorad Laboratories Co., Ltd.) in a conventional manner to prepare SP-322-bound agarose and t-PA is then purified in a conventional manner of either column method or batch method.

Anti-t-PA monoclonal antibody SP-322 can be used as a reagent in enzyme immunoassay (EIA) and radioimmunoassay (RIA). In the enzyme immunoassay, SP-322 is firstly coated onto a solid phase such as a microtiter plate, etc. and blocked with bovine serum albumin, etc. Then, a sample containing a known or unknown amount of t-PA is added thereto in a predetermined amount to effectively adsorb t-PA in the sample via the antibody. An enzyme labeled or biotin-bound anti-t-PA antibody is added to the system to form a color or light using a chromogenic or light-emitting substrate for the enzyme or enzyme labeled avidin and its substrate. t-PA concentration in the sample is calibrated by the standard curve previously obtained by using standard t-PA thereby to quantitatively determine t-PA.

Further in the SP-322 anti-t-PA monoclonal antibody, t-PA is adsorbed to a microtiter plate, etc. coated with SP-322 and the activity is measured by direct method, namely, by reacting with chromogenic substrate specific to t-PA. Alternatively, the activity is measured by indirect method, namely, by firstly converting plasminogen into plasmin and decomposing a chromogenic substance specific to plasmin with the plasmin produced to form a color. t-PA concentration in the sample is calibrated by the standard curve previously obtained by using standard t-PA.

EXAMPLES

Hereafter the present invention will be described in more detail by referring to the examples.

Measurement 1

Anti-t-PA monoclonal antibody SP-322 was adjusted to 1 μg/ml with 50 mM carbonate buffer (pH 9.6) and 200 μl each was separately added to a microplate (Linbro ® EIA plate, Flow Laboratories, Inc.). The microplate was allowed to stand at room temperature for 4 hours or at 4° C. overnight.

The content in wells was removed by suction and 200 μl each of 10 mM Tris-HCl buffer (pH 7.4) supplemented with 150 mM sodium chloride (Kanto Chemical Co., Ltd.), 1% bovine serum albumin (Sigma, A-7030) and 0.02% sodium azide was separately added into wells. The plate was allowed to stand at room temperature for an hour or at 4° C. overnight.

The content in the wells was removed by suction and the wells were washed 4 times with 300 μl of 10 mM Tris-HCl buffer (pH 7.4) supplemented with 0.05% Tween 20 (Nakarai Chemicals Co., Ltd.) ( Buffer I).

Immediately thereafter, 200 μl each of a sample (whole blood or diluted blood) containing t-PA was separately added followed by reacting at room temperature for 10 minutes.

The content in the wells was removed by suction and the wells were washed 6 times with 300 μl of Buffer I.

Figure 3:
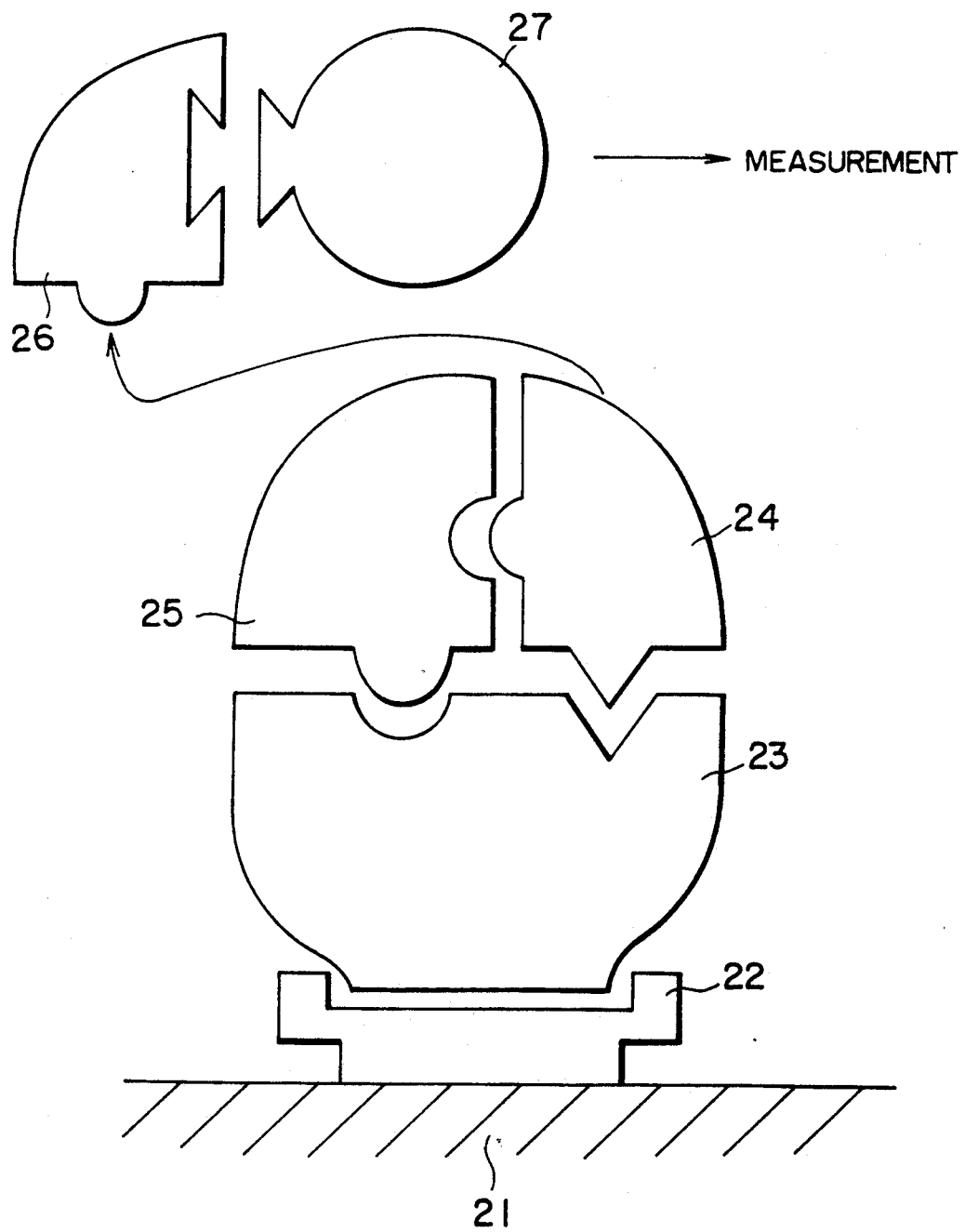
FIG. 3 is a drawing showing the principle of an example of the measurement method; wherein numeral 21 denotes a solid phase, numeral 22 denotes an anti t-PA-antibody IgG fraction, numeral 23 denotes t-PA, numeral 24 denotes plasminogen, numeral 25 denotes stimulator, numeral 26 denotes plasmin and numeral 27 denotes chromogenic peptide substrate.
Figure 4:
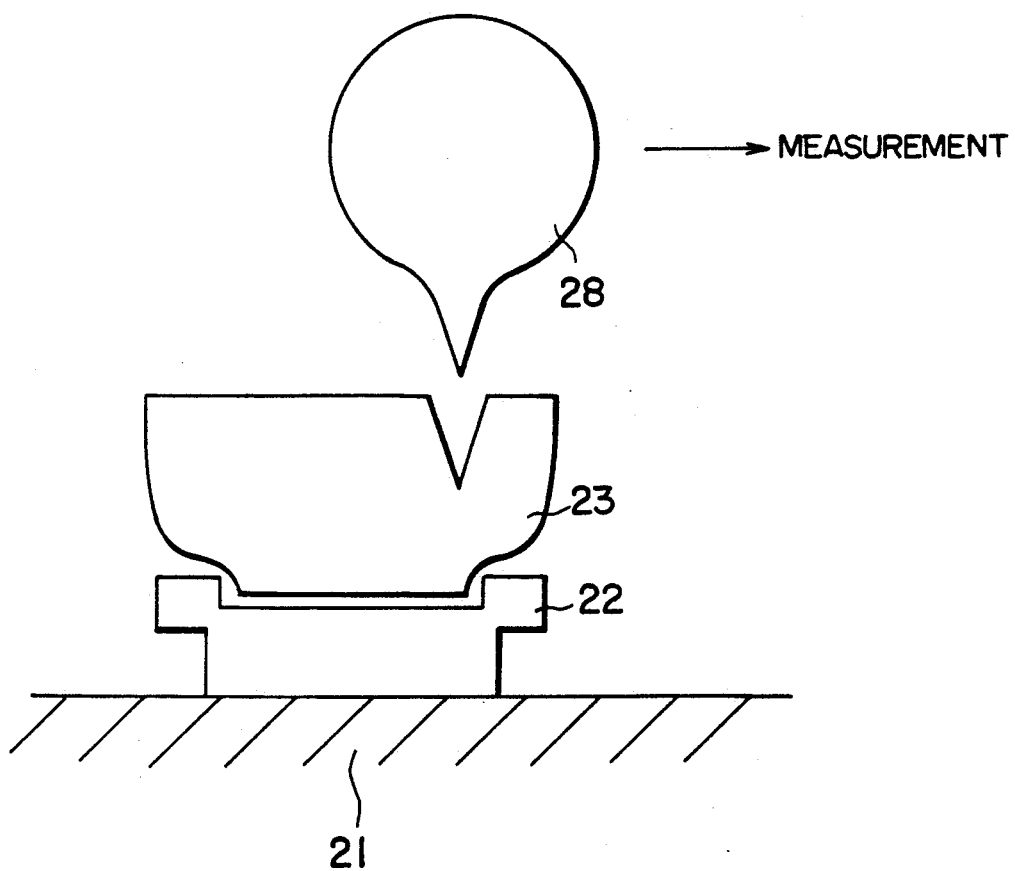
FIG. 4 is a drawing showing the principle of a method for measurement of t-PA activity of the product directly with a chromogenic peptide substrate wherein numeral 21 denotes a solid phase, numeral 22 denotes an anti t-PA-antibody IgG fragment, numeral 23 denotes t-PA and numeral 28 denotes chromogenic peptide substrate.

Next, 200 μl each of 20 mM Tris-hydrochloride buffer (pH 7.4) supplemented with 0.45 mM S-2251 (manufactured by Kabi Co., Ltd.), 150 mM sodium chloride, 0.01% Tween 80 (manufactured by Nakarai Chemicals Co., Ltd.), 0.042 μM lysine-plasminogen and 120 μg/ml cyanogen bromide-treated fibrinogen was separately added into wells as substrate buffer. After incubation at 37° C. for 90 minutes, the reaction was stopped by adding 50 μl of 50% acetic acid aqueous solution, and t-PA activity was determined by absorbancy at 405 nm with a spectrophotometer (Titertek ® Multiskan Type 310C). (A chart of its principle is shown in FIG. 3. Further a chart of principle for directly determining t-PA activity with chromogenic peptide substrate is shown in FIG. 4.)

Preparations of lysine-plasminogen, cyanogen bromide-treated fibrinogen and anti-t-PA monoclonal antibody SP-322 are as follows.

Preparation of lysine-plasminogen

Lysine-plasminogen (manufactured by The Green Cross Corporation, Code No. 1089) (2100 CU) was dissolved in pure water. In order to fully inactivate plasmin contained, 20 ml of 20,000 KI/ml aprotinin (Sigma Corp., No. A-6012) was added in an excess amount and the system was allowed to stand at 4° C. overnight. Biogel P100 Gel (BIO RAD) was equilibrated with 20 mM Tris-hydrochloride buffer (pH 7.5) supplemented with 140 mM sodium chloride. After eluting with the same buffer, the peak of lysine-plasminogen was fractionated. An amount of protein obtained in this run was 100 mg. Lysine-plasminogen thus obtained was separately kept frozen at −20° C. until use.

Preparation of cyanogen bromide-treated fibrinogen

Preparation was performed according to the method of C. Zammarron [J. Biol. Chem., 259, No. 4, 2080–2083 (1984)].

0.8 g human fibrinogen was dissolved in 70% formic acid containing 1.3 g of cyanogen bromide. The solution was incubated at room temperature for 17 hours in nitrogen gas. Then, the mixture was dialyzed against 30 liters of pure water for 24 hours. Further 5 liters of pure water was added thereto followed by dialysis. Thus, cyanogen bromide-treated fibrinogen was prepared.

An amount of protein obtained in this run was 700 mg. The obtained cyanogen bromide-treated fibrinogen was separately kept frozen at $-20°$ C. until use.

Preparation of anti-t-PA monoclonal antibody

I. Preparation of hybridoma SP-322 a) Preparation of immunized spleen cell

An emulsion obtained by mixing purified human melanoma cell-derived t-PA (manufactured by Bioscott Co., Ltd.) with the same volume of Freund's complete adjuvant was intraperitoneally administered to BALB/C strain female mice (8 week old at the onset of immunization) in a dose of 30 μg/mouse or 7.5 μg/mouse (first immunization). Subsequently, an emulsion obtained by mixing 30 μg/mouse or 7.5 μg/mouse of t-PA with the same volume of Freund's incomplete adjuvant was intraperitoneally injected twice at intervals of 3 to 4 weeks. Six weeks after the third immunization, 0.4 ml of physiological saline containing 30 μg/mouse or 7.5 μg/mouse of t-PA was intraperitoneally administered (final immunization). Three days after the final immunization, spleen cells were collected from 2 mice and suspended in DMEM medium. Red blood cells were removed by treating with 0.17M ammonium chloride at $0°$ C. for 10 minutes followed by centrifugation.

b) Preparation of hybridoma SP-322

The spleen cells ($5 \times 10^8$) prepared as described above were fused with mouse myeloma cells P3X63 Ag8.U1 (P3U1) ($1 \times 10^8$) according to the method of Köhler and Milstein [Nature, 256, 495 (1975)]. That is, spleen cells and P3U1 cells were washed with DMEM several times. Then, both were mixed in a 50 ml plastic test tube containing fresh DMEM.

Then, centrifugation was performed to remove the medium. While stirring, 1 ml of DMEM containing 50% (w/v) polyethylene glycol (manufactured by Sigma Corporation, mean molecular weight of 3640) kept at $37°$ C. was gradually added over a minute. Next, 10 ml of DMEM kept at $37°$ C. was dropwise added to complete the cell fusion.

The cell suspension was centrifuged. After the supernatant was removed, HAT medium [DMEM medium containing 10% bovine fetal serum supplemented with hypoxanthine ($1 \times 10^{-4}$M), aminopterine ($4 \times 10^{-7}$M) and thymdine ($1.6 \times 10^{-5}$M)] was added to the cell pellet to adjust a spleen cell concentration to $5 \times 10^5$ cells/ml. 2 ml of this cell suspension was plated in a 24 well plastic plate (spleen cells, $1 \times 10^6$/well ). The half of the medium was removed by suction every 4 to 5 other days and the aforesaid HAT medium was replenished. Seven to ten days after the cell fusion, growth of hybridoma was observed in all of the wells, where anti-t-PA activity in the culture supernatant was determined by the immuno precipitation method.

c) Measurement of anti-t-PA activity in the supernatant by immuno precipitation method Radioactive iodine ($^{125}$I)-labeled (by chloramine T method) t-PA [100 μl, dissolved in 25 mM Tris buffer, pH 7.4, containing 0.7% bovine serum albumin, 0.3M sodium chloride and 0.05% (w/v) Tween 80; hereafter simply referred to as $^{125}$I-t-PA] was mixed with 20 μl of hybridoma culture supernatant. After allowing to stand in a plastic tube at room temperature overnight, 1 μl of rabbit anti-mouse IgG anti-serum was added to the mixture. Then the mixture was allowed to stand at room temperature for further 3 hours.

Ten microliters of Pansorbin (trademark, manufactured by Calbiochem Co., Ltd.) were added to the mixture. Thirty minutes after mixing, 2 ml of Tris buffer was added thereto. The mixture was immediately centrifuged (3000 rpm, 15 minutes). The supernatant was removed and radioactivity of $^{125}$I-t-PA in the precipitate was counted by an Autowell Gamma Counter Model ARC 300 manufactured by Aloca Co., Ltd. With respect to hybridoma-grown wells showing significant $^{125}$I-t-PA immune precipitation, further cellular proliferation was performed in DMEM medium to effect single cell cloning. Cloning was conducted twice by limited dilution method using a 96 well microplate in which BALB/C mouse thymocytes ($10^6$ cells/well) were used as feeder cells. The hybridoma clone thus obtained was named SP-322. Anti-t-PA monoclonal antibody produced by hybridoma SP-322 was also named SP-322.

II. Production and purification of monoclonal antibody

After 0.5 ml of 2,6,10,14-tetramethylpentadecane (Pristan, manufactured by Aldrich Co., Ltd.) was intraperitoneally injected to BALB/C strain male mice of 6 to 8 week old, a suspension of $10^7$ hybridoma SP-322 cells in 0.5 ml of physiological saline was intraperitoneally injected after 7 to 14 days. Following 10 to 20 days the ascitic fluids were collected from the mice. Each animal gave 5 to 10 ml of the ascitic fluids containing monoclonal antibody. The ascitic fluids was centrifuged to remove insoluble matters. Then, an equivolume of saturated ammonium sulfate solution was added to the supernatant. The mixture was allowed to stand at $4°$ C. for an hour to overnight. The precipitates were collected by centrifugation and redissolved in 0.1M phosphate buffer, pH 8, containing of 0.9% sodium chloride. The solution was then dialyzed against 100-fold volume of the same buffer (γ-globulin fraction). IgG was purified from this fraction utilizing a kit for purification of MAPS-II mouse monoclonal antibody (trademark, manufactured by Biorad Laboratories). Namely, the equal volume of binding buffer was added to the γ-globulin fraction. After mixing them, the mixture was applied to a column (gelbed volume, 5 or 10 ml) packed with Affigel Protein A (manufactured by Bio Rad Laboratories) or protein A Sepharose CL4B (manufactured by Pharmacia Fine Chemicals, Inc.), which had been sufficiently pre-equilibrated with the same binding buffer followed by washing with the binding buffer 10-column volume. Then, IgG was eluted in approximately 3-column volume of elution buffer contained in the kit. The eluted IgG fraction was concentrated by salting out with ammonium sulfate. The concentrate was dialyzed against 0.01 to 0.1M phosphate buffer containing 0.9% sodium chloride, which was named as IgG standard of SP-322. In general, 11 to 18 mg of IgG was obtained per 1 ml of the ascitic fluids.

Physicochemical properties of monoclonal antibody

The following physicochemical properties were determined using the IgG fraction of monoclonal antibody SP-322 purified as in II, except for item b).

a) Molecular weight: 153,000 ($\pm 10,000$)

SDS polyacrylamide gel electrophoresis was conducted on a 9% or 12% slab gel using the buffer system of Laemli [Nature, 227, 680 (1970)] thereby to estimate a molecular weight of the antibody. As a molecular weight marker, an electrophoresis molecular weight calibration kit (low molecular weight kit; phosphorylase b, 94,000; bovine serum albumin, 67,000; ovalbumin, 43,000; carbonic anhydrase, 30,000; trypsin inhibitor, 20,100; α-lactalbumin, 14,400) manufactured by Pharmacia Fine Chemicals was used.

b) IgG subclass: IgG 1

Using the hybridoma culture supernatant, IgG subclass of SP-322 was determined by a kit for typing mouse monoclonal antibody manufactured by Serotech Co., Ltd. This is accomplished by double immunodiffusion method of Ouchterlony in which 75 μl of the supernatant was applied in a well at the center and 10 μl of various anti-mouse immunoglubulin antibodies were added into wells at the periphery. After allowing to stand at room temperature for 24 hours, formation of precipitates in lines due to antigen-antibody complex was observed.

c) Amino acid sequence (amino terminal end ): L-chain: Asp-Ile-Val-Leu-Thr-Gln-Ser-Pro-Ala-Ser-Leu-Ala-Val-Ser Sequence analysis of L-chain and H-chain of IgG at the amino terminal end thereof was conducted by Edman's degradation method [Edman et al., European J. Biochem., 1, 80 (1967)]. L-chain and H-chain of the antibody IgG molecule were separated from each other by SDS-polyacrylamide gel electrophoresis, etc. under reducing condition. Each chain was recovered from the gel by electroelution. Then, after purifying by reversed phase high performance liquid chromatography, each chain was analyzed by a gas phase sequencer (Model 470A; manufactured by Applied Biosystems Co., Ltd.,), whereby coupling, peptide bond cleavage and PTH (phenyl hydantoin)-labeled amino acid formation were carried out. The obtained PTH amino acids were separated and analyzed by isolated with Model 120 A PTH Analyzer manufactured by Applied Biosystems Co., Ltd. directly connected to the sequencer. By comparing with retention time of standard PTH-amino acid, each PTH-amino acid was identified.

As the result, 14 amino acid residues from the amino terminal end having the sequence described above were identified with L-chain. On the other hand, H-chain failed to determine its sequence directly from the amino terminal end by the method described above; this is considered that regarding H-chain, there would be a possibility of the amino terminal end being blocked in any mode.

d) Affinity to antigen

Figure 10:
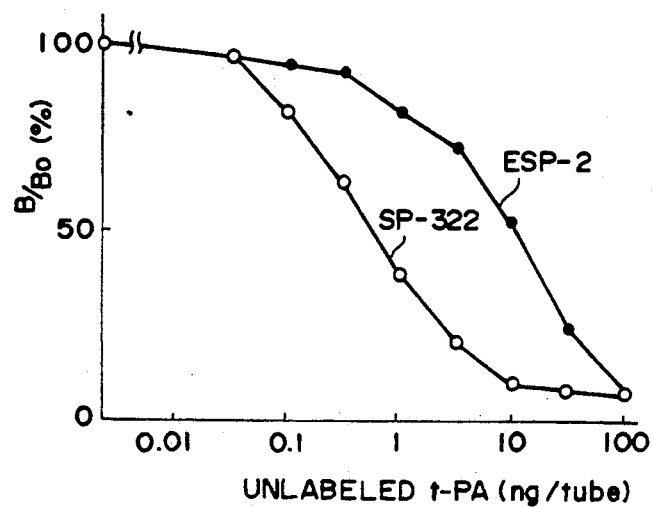
FIG. 10 shows curves for inhibition of unlabeled t-PA having various concentrations in immuno precipitation reaction of $^{125}$I-t-PA with various antibodies wherein -o- denotes SP-322 and -•- denotes ESP-2.

Affinity to antigen was determined as follows. In the immuno precipitation reaction using SP-322 of the aforesaid $^{125}$I-labeled t-PA, unlabeled t-PA was added in various concentrations to cause competition, whereby an inhibition curve was obtained (FIG. 10). A dissociation constant was roughly estimated from the concentration of unlabeled t-PA which gives 50% inhibition. The dissociation constant of monoclonal antibody SP-322 was estimated to have affinity higher by approximately 20 to 40 times than that of anti-t-PA monoclonal antibody ESP-2 manufactured by Bioscott Co., Ltd. This affinity is comparable to that of polyclonal antibody #387 (manufactured by American Diagnostica Co., Ltd.) which has the highest affinity to antigen.

Figure 11:
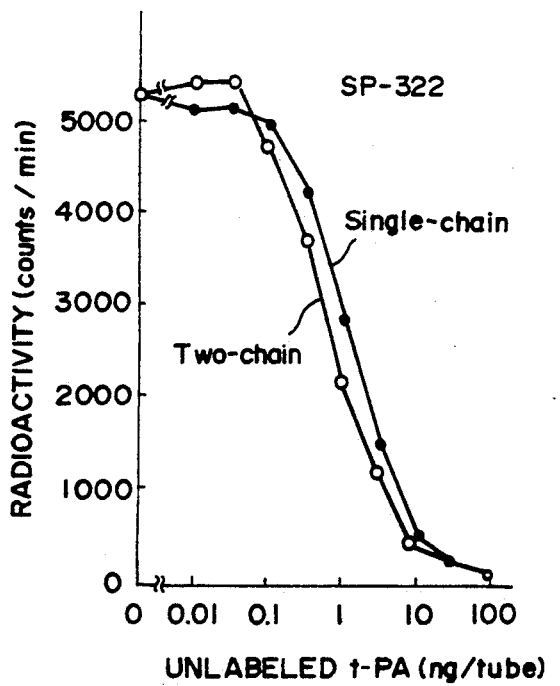
FIG. 11 shows curves for inhibition of single-chain- or two-chain-type unlabeled t-PA in immuno precipitation reaction of $^{125}$I-t-PA with monoclonal antibody SP-322 wherein -o- denotes two-chain and -•- denotes single-chain.

Further a difference in affinity of the monoclonal antibody of the present invention depending upon a difference in t-PA chain was examined using single-chain- and two-chain-type human melanoma cell-derived t-PAs manufactured by American Diagnostica Co., Ltd. The difference was determined by inhibition curves obtained when 1 to 100 ng/tube of single-chain or two-chain t-PA was applied in the aforesaid immuno precipitation reaction of $^{125}$I-t-PA. As shown in FIG. 11, it was estimated that SP-322 had almost equal affinity to both single-chain and two-chain t-PAs.

e) Influence of monoclonal antibody SP-322 to fibrinolytic activity of t-PA

Influence of SP-322 on fibrinolytic activity of t-PA was examined in vitro by $^{125}$I-labeled fibrin film lysis method. The $^{125}$I-labeled fibrin film lysis method was conducted as described by Hoyraerts et al. [J. Biol. Chem., 257, 2912 (1982)]. That is, an adequate amount of $^{125}$I-fibrinogen (manufactured by Commissariat A L'energie Atomique Co., Ltd.) was mixed with 1.8 μM fibrinogen. 5 μl/well of the mixture was applied to a 96 well microtiter plate ( Limbro) and dried at 40° C. overnight, followed by addition of 100 μl each of 1.6 μ/ml thrombin (manufactured by Mochida Pharmaceutical Co., Ltd.). The plate was allowed to stand for 4 hours at 37° C. to complete fibrination. After the plate was washed twice with 10 mM phosphate buffer containing 0.2% bovine serum albumin and 0.9% sodium chloride, it was provided for assay of activity. In each well, 50 μl of 200 nM plasminogen was applied and 50 μl of either standard t-PA or unknown sample was added.

After mixing them, the reaction was carried out at 37° C. for 2 hours. From each well, 50 μl was taken and $^{125}$I-fibrin lyzed was counted by an auto well gamma counter manufactured by Aloca Co., Ltd. The fibrinolytic activity of t-PA was quantitatively determined by calibrating from the standard curve obtained using standard t-PA. The standard t-PA used is human melanoma cell-derived t-PA purchased from Bioscott Co., Ltd. which was standardized according to the International t-PA Standard [Gaffney and Curtis, Thromb. Haemostas., 53, 134 (1985)].

Figure 12:
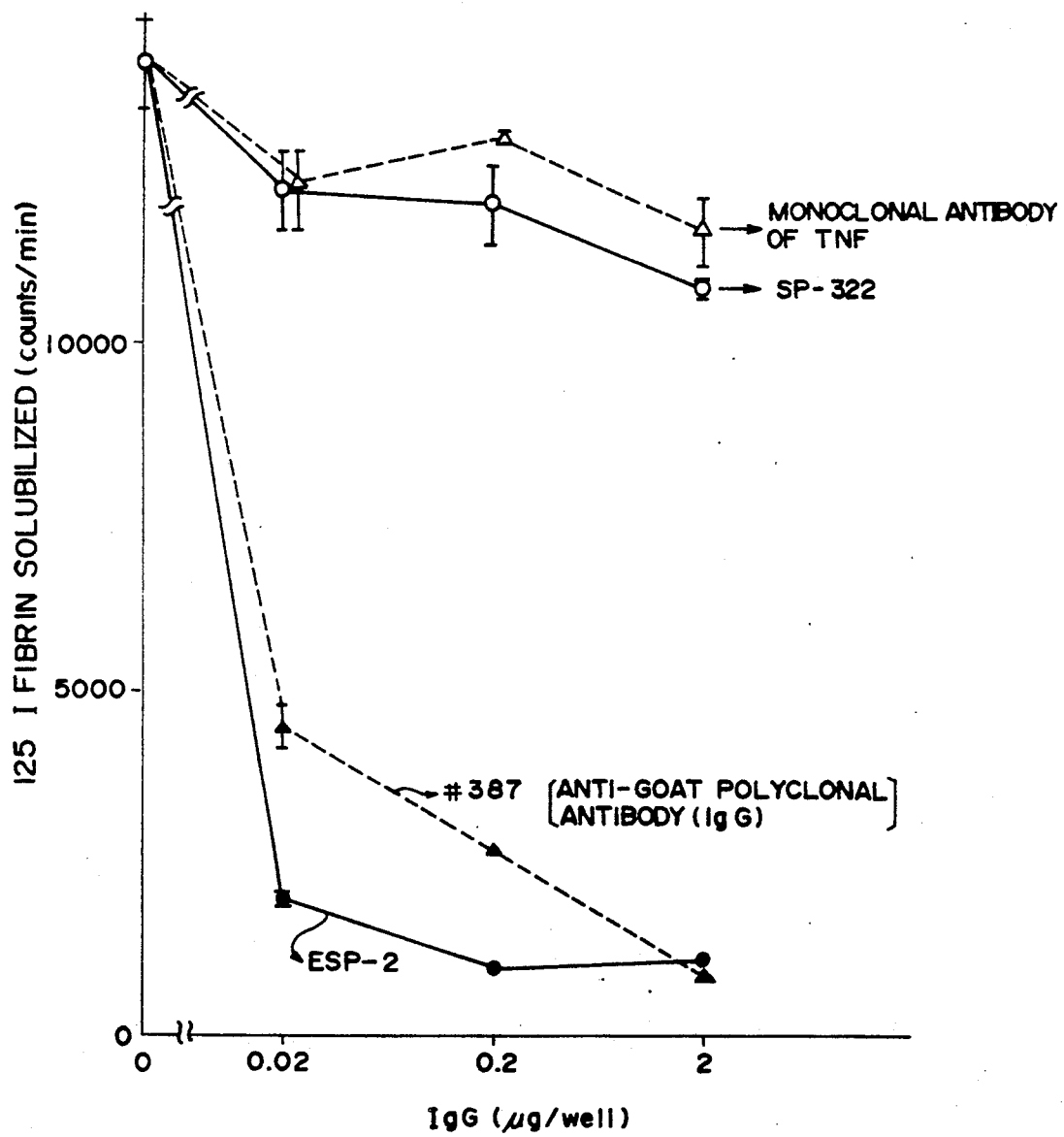
FIG. 12 is a drawing showing inhibition effect of t-PA activity by various antibodies using $^{125}$I-fibrin film lysis method; wherein --△-- is monoclonal antibody for control, -o- is SP-322, --▲-- is #387 (anti-goat polyclonal antibody IgG) and -•- is ESP-2.

The activity value of t-PA (5 u/ml) which had been previously incubated with 0.8 to 80 μg/ml SP-322 at room temperature overnight was measured. As shown in FIG. 12, some reduction (approximately 15%) of the activity was noted but there was no significant difference from that of monoclonal antibody unbound to t-PA (anti-human tumor necrosis factor antibody) used as a control. On the contrary, polyclonal anti-t-PA antibody (goat, manufactured by American Diagnostica Co., Ltd.) or monoclonal antibody ESP-2 manufactured by Bioscott Co., Ltd. showed remarkable inhibition of the activity even at the minimum dose.

f) Antigen binding site

Figure 13:
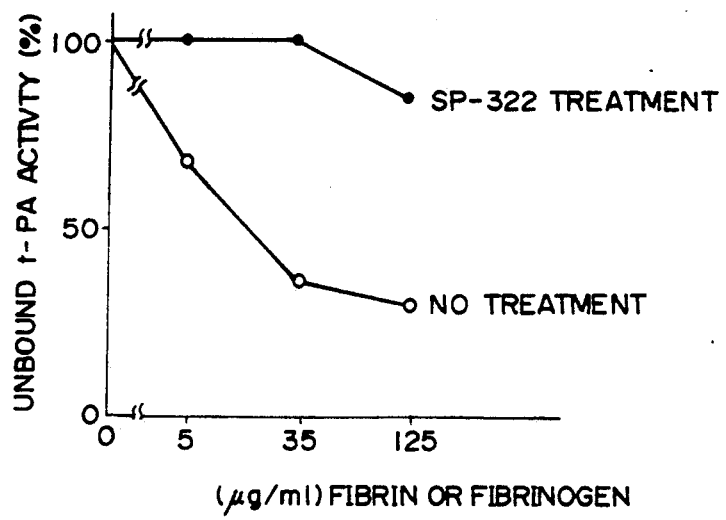
FIG. 13 shows fibrin-unbound t-PA activity which indicates influence of fibrin affinity of t-PA by monoclonal antibody SP-322 wherein -•- is pretreated with SP-322 and -o- is non-treated.

After t-PA and SP-322 were incubated at room temperature for 10 hours in a weight ratio of 1:1000, affinity of t-PA to fibrin was examined by the method of Verheijen [EMBO. J., 5, 3525 (1986)]. To a mixture of t-PA (final concentration, 2 μg/ml) and fibrinogen (final concentration, 1 to 125 μg/ml), 1 u of thrombin was added. The mixture was stirred and allowed to stand at room temperature for 3 minutes to form fibrin. Then, the tube was centrifuged (16,000, rpm, 8 minutes) and activity of fibrin-unbound t-PA in the supernatant was determined by fibrin plating method. In the fibrin plating method, SP-322 does not greatly inhibit t-PA activity. As shown in FIG. 13, binding to fibrin was greatly inhibited when the t-PA was pretreated with SP-322. It is assumed that SP-322 would have a binding site at or near the fibrin affinity site of t-PA but would not bind to the active site of t-PA.

g) Cross reactivity with urokinase

Figure 14:
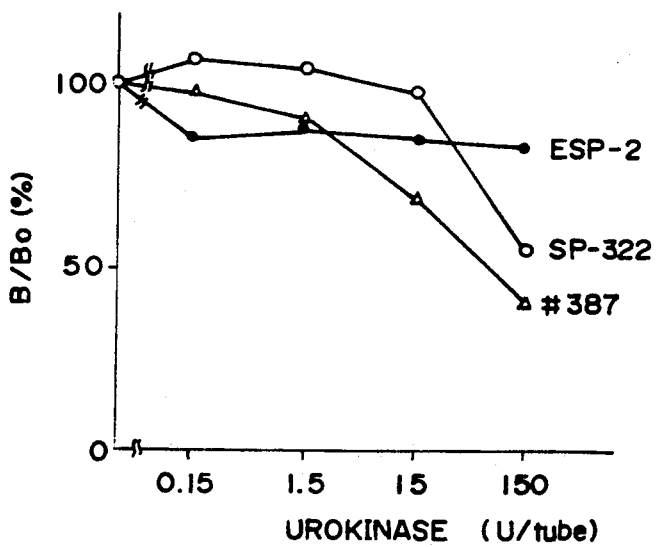
FIG. 14 indicates curves showing influence of urokinase on immuno precipitation reaction of $^{125}$I-t-PA with monoclonal antibody SP-322 or other anti-t-PA antibodies wherein -o- denotes SP-322, -•- denotes ESP-2 and -△- is #387.

Cross reactivity between SP-322 and urokinase (manufactured by The Green Cross Corporation) was examined by the aforesaid immuno precipitation reaction and $^{125}$I-fibrin film lysis method. In the immuno precipitation reaction, cross-reactivity was determined by an inhibitory effect of urokinase against immuno precipitation of $^{125}$I-t-PA with SP-322. The inhibition was observed by 44% only in the case of adding 150 u/tube urokinase (FIG. 14). When compared with the inhibitory curves with t-PA (FIG. 10), cross-reactivity of urokinase was determined to be about 0.1% of t-PA. Further in the $^{125}$I-fibrin film lysis method, SP-322 did not inhibit urokinase activity (3 u/ml) at all in concentrations up to 80 μg/ml.

Standardization

Using 0.02 to 40 ng/ml of t-PA single-chain standard samples, a calibration curve was obtained. Dilution was performed with Buffer I supplemented with 0.25% bovine serum albumin.

The results revealed that a calibration curve was effective in the range from 0.03 to 20 ng/ml.

Measurement of t-PA activity in blood samples of healthy volunteers

Healthy volunteers were kept for 10 minutes at rest. After tightly fastening the upper arm for 5 minutes under pressure of 100 mmHg, the Antecubital vein was punctured. Blood samples were collected in 1/10 volume of 3.8% sodium citrate (The Green Cross Corporation). After blood collection, blood samples were transferred to test tube which had been kept in ice. Immediately thereafter, 200 μl of whole blood sample was separately applied to a microplate coated with antibody which had been previously prepared, and was processed for assay as described above. The results are shown in Table 1.

TABLE 1

| No. | Age | t-PA activity (ng/ml) | No. | Age | t-PA activity (ng/ml) |
|---|---|---|---|---|---|
| *1 | 26 | 0.34 ± 0.02 | **6 | 25 | 0.02 |
| 2 | 28 | 0.30 ± 0.01 | 7 | 26 | 0.16 ± 0 |
| 3 | 31 | 0.17 ± 0.01 | 8 | 34 | 0.05 ± 0 |
| 4 | 34 | 0.81 ± 0.01 | 9 | 43 | 0.08 ± 0 |
| 5 | 37 | 1.22 ± 0.44 | 10 | 47 | 0.42 ± 0.02 |
| mean x̄ | | 0.57 | mean x̄ | | 0.15 |

*Nos. 1 to 5: blood taken under 100 mmHg pressure for 5 min.
**Nos. 6 to 10: blood taken normally.

For reference, 1 ng/ml of t-PA activity corresponds to 0.55 IU/ml.

Measurement 2

Preparation of dipstick

A polystyrene plastic stick (manufactured by Nippon Soda Co., Ltd., depth of 100 mm, width of 5.5 mm and thickness of 1 mm) was dipped overnight in a water bath containing 20-fold diluted Extran MA 01 ® (trademark, manufactured by Merck Inc.) at 60° C. After washing the stick with a ultrasonic washing machine for 3 hours and with tap water for 3 hours, the stick was dipped in distilled water overnight. The stick was dried by a drier at 40° C. and a slit as a broken area was made at 10 mm from the tip of the stick on both surfaces. Anti-t-PA monoclonal antibody SP-322 was adjusted to 1 μg/ml with 50 mM carbonate buffer (pH 9.6) and 200 μl each was separately applied to a PPN Tube ® (trademark, manufactured by Dainippon Pharmaceutical Co., Ltd.). Then the stick was put in the tube, and the tube was allowed to stand at room temperature for 4 hours or at 4° C. overnight to coat the antibody onto the stick. The coated stick was put into a PPN Tube in which 500 μl each of 10 mM Tris-hydrochloride buffer (pH 7.4) containing 150 mM sodium chloride, 1% bovine serum albumin (manufactured by Sigma) and 0.02% sodium azide. Again the tube was allowed to stand at room temperature for 4 hours or at 4° C. overnight to block the surface thereof. The stick was washed with Buffer I as described above and stored in Buffer I at 4° C.

This stick which was coated and blocked was stable for over the period of longer than 3 months when stored in the buffer at 4° C.

Measurement of t-PA activity in healthy volunteer's blood samples using the dipstick 1) Measurement of t-PA activity using whole blood sample From the Antecubital vein of the volunteers, blood was collected in a vacutainer tube containing 3.13% sodium citrate in such that a ratio of sodium citrate and blood sample was 1:9. Immediately after blood collection, the aforesaid stick previously prepared which was coated with anti-t-PA monoclonal antibody and blocked was transferred to the vacutainer tube to react at room temperature for 10 minutes. The stick was taken out, washed with Buffer I and applied to a microplate. Using a well of the microplate as a support, the stick was broken and only the stick portion including the anti-t-PA monoclonal antibody coated area was kept in the microplate.

Then, 200 μl each of 20 mM Tris-hydrochloride buffer (pH 7.4) supplemented with 0.45 mM S-2251 (manufactured by Kabi Co., Ltd.), 150 mM sodium chloride, 0.01% Tween 80 (manufactured by Nakarai Chemicals Co., Ltd.), 0.042 μM lysine-plasminogen and 120 μg/ml cyanogen bromide-treated fibrinogen was separately applied to the wells of the microplate as a substrate buffer. After incubation at 37° C. for 17 hours, the stick was removed and the aliquot was measured at 405 nm with a spectrophotometer Multiskan Type 310C [Titertek] to determine t-PA activity.

It may be possible to use 50 μl of 50% acetic acid aqueous solution to stop the reaction, however, no acetic acid aqueous solution was used in this particular experiment.

2) Measurement of t-PA activity using diluted blood sample

After blood collection as in 1), 0.5 ml of blood sample was immediately applied to a test tube containing the previously prepared stick coated with anti-t-PA monoclonal antibody and blocked and 1.5 ml of Buffer I. The test tube was allowed to stand at room temperature for 60 minutes.

Subsequently, t-PA activity in diluted blood sample was determined in a manner similar to 1) except that the reaction with the substrate buffer was performed for 4 hours.

Further, t-PA activity in blood sample could also be determined by collecting 0.45 ml of blood with the vacutainer tube which previously contained 1.5 ml of Buffer I, 0.05 ml of anticoagulant and the stick described above. This method is particularly excellent in that the reaction can be performed immediately after blood collection. The data described below are those obtained using the vacutainer tube described above.

Standardization

Standardization was performed also in the stick methods 1) and 2) as in Measurement 1.

Figure 5:
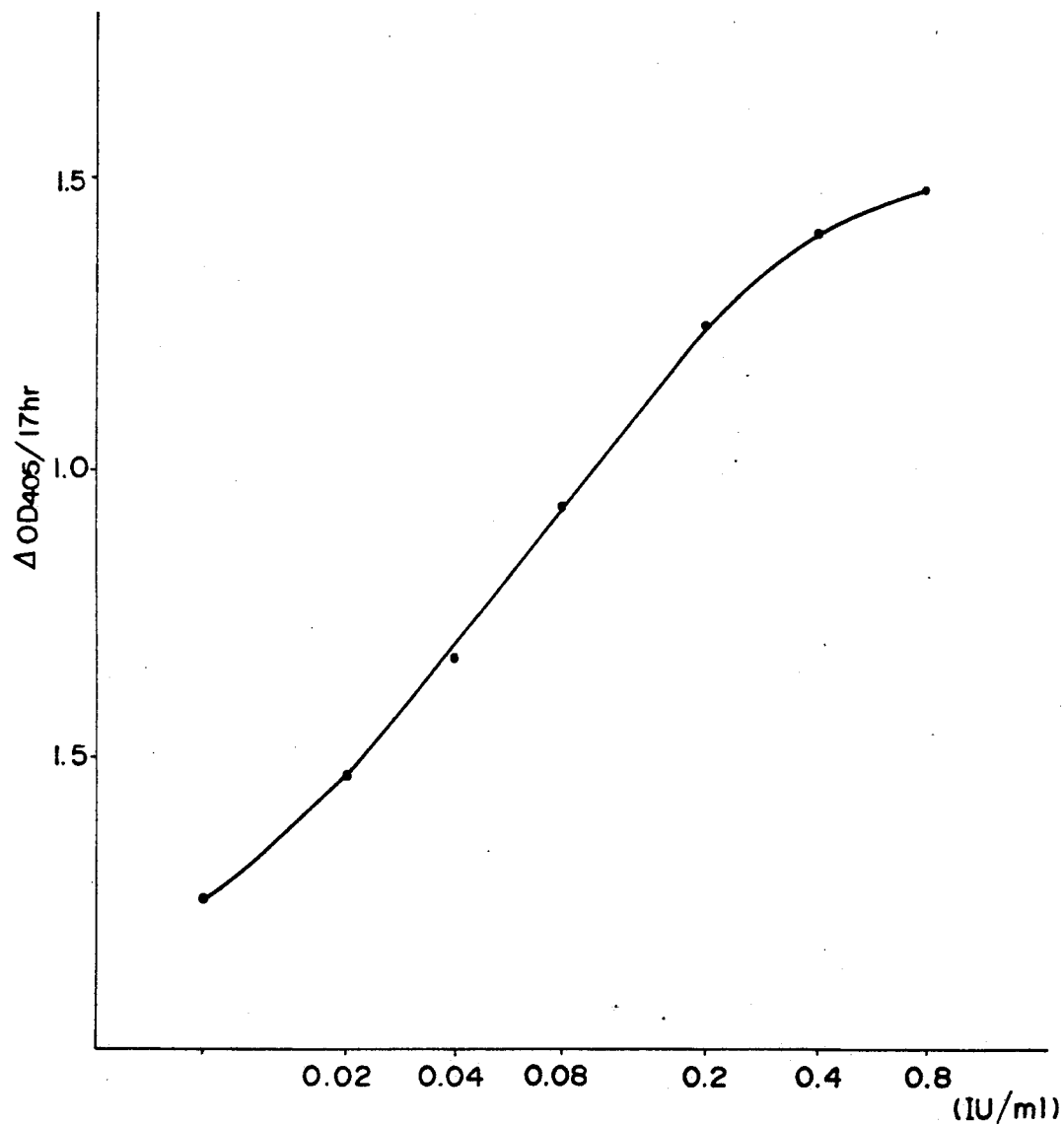
FIGS. 5 and 6 show calibration curves in semilogarithmic scale of a standard sample of whole blood and a standard sample of diluted blood obtained using a stick.
Figure 6:
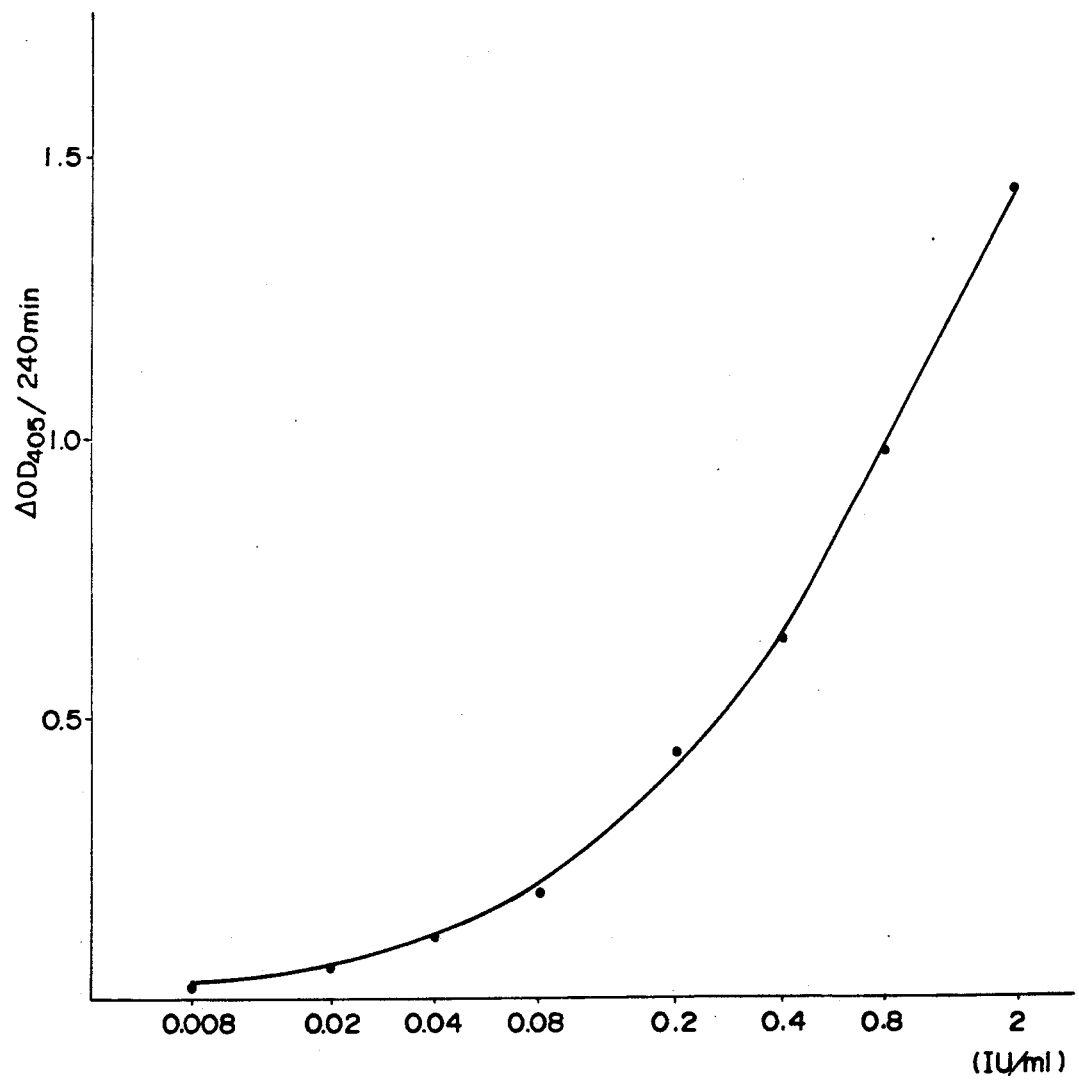
Figure 7:
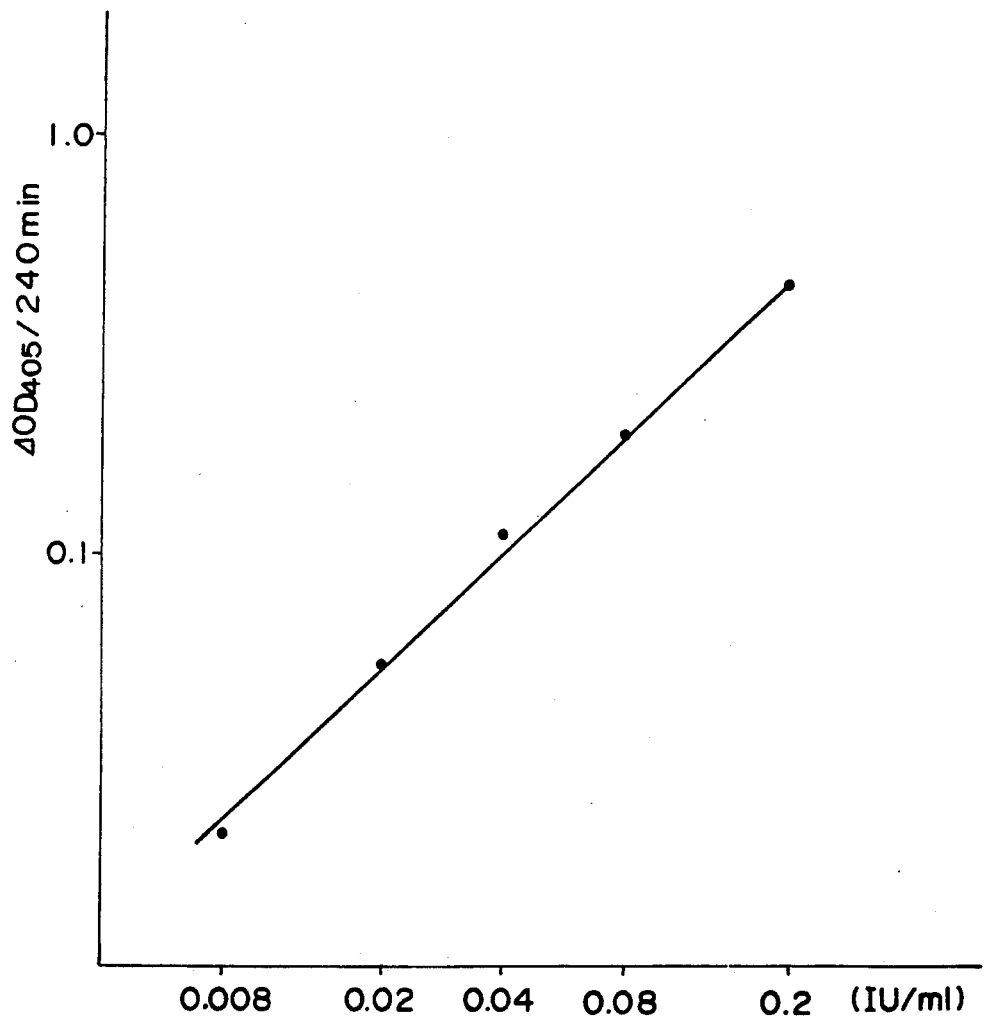
FIG. 7 shows a calibration curve obtained by correcting the calibration curves shown in FIGS. 5 and 6 to a linear function.

FIGS. 5, 6 and 7 show 1), namely, a calibration curve of semilogarithmic scale obtained by the whole blood method using the stick, 2), a calibration curve of semilogarithmic scale obtained by the diluted blood method using the stick and, a calibration curve of linear function obtained by the method 2), respectively.

As can be seen from these curves, it is evident that any of the measurement methods 1) and 2) could be effective as calibration curves in the range from 0.008 to 2 IU/ml.

Results of measurement for t-PA activity in healthy volunteer's blood samples

Figure 8:
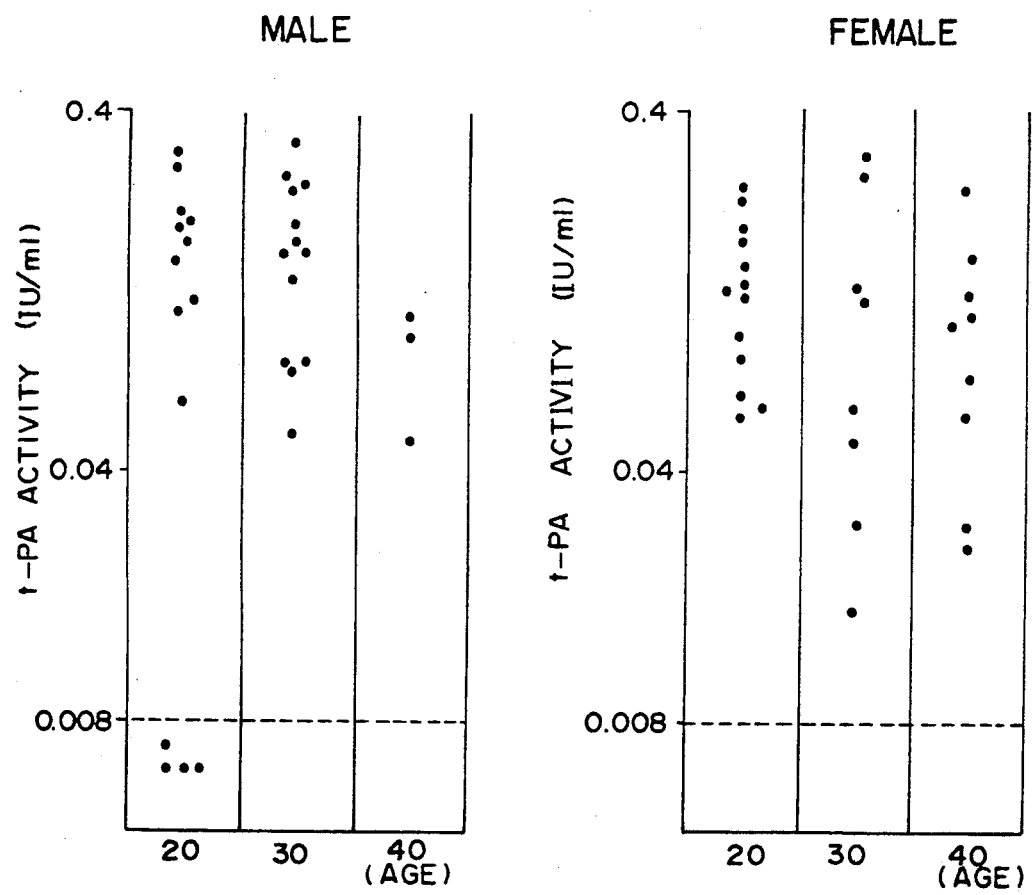
FIG. 8 shows measurement results of whole blood using a stick.
Figure 9:
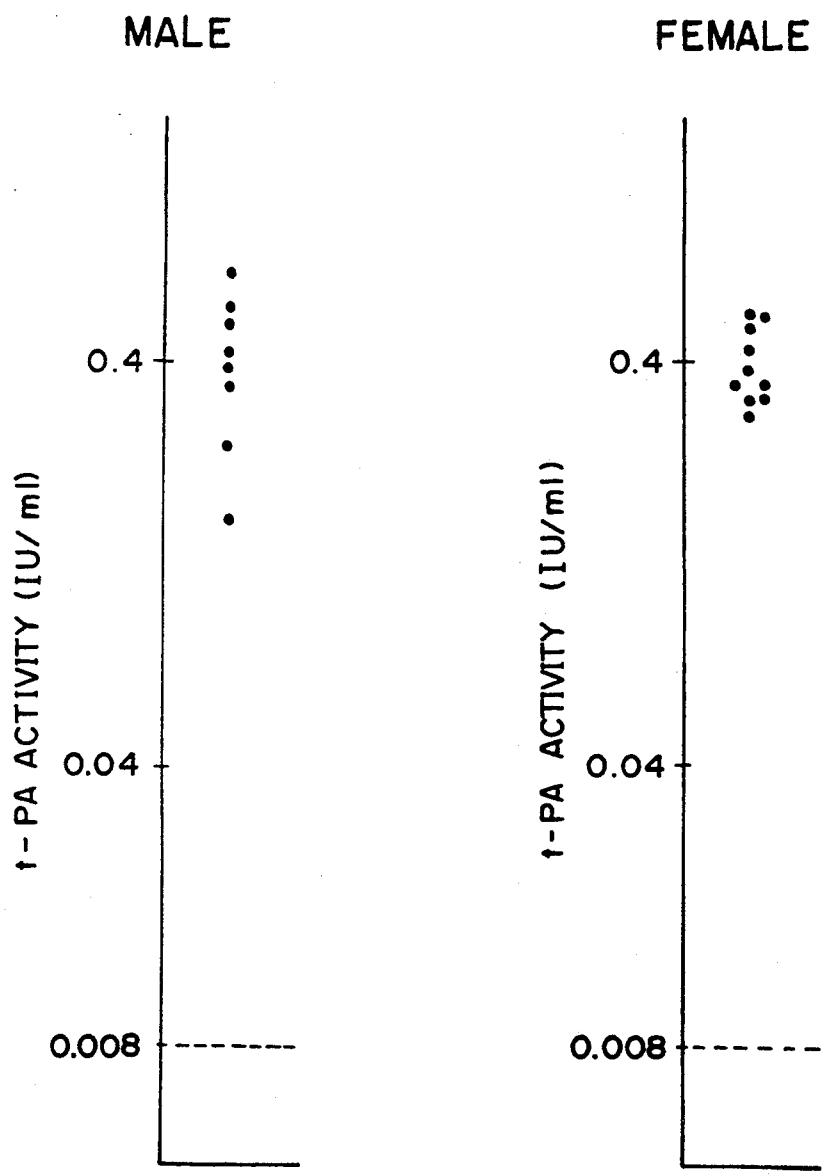
FIG. 9 shows measurement results of its diluted blood.

The results obtained by the method using whole blood sample described above are shown in FIG. 8 and the results obtained using diluted blood sample are shown in FIG. 9.

The results revealed that true t-PA activity in blood sample can be measured by ordinary blood collection and the method of the present invention, especially the dipstick method, is much more excellent than conventional methods.

What is claimed is:

1. A method for measurement of a tissue plasminogen activator activity which comprises reacting a solid phase having bound thereto anti-tissue plasminogen activator antibody IgG fraction having affinity to a site other than the active site of a tissue plasminogen activator with the tissue plasminogen activator in whole blood or diluted blood and then determining an enzymatic activity of the reaction product.

2. The method as claimed in claim 1, wherein said activity of the product is determined by reacting the product with a chromogenic peptide substrate specific to the tissue plasminogen activator and measuring an amount of a substance released form the chromogenic peptide substrate.

3. The method as claimed in claim 1, wherein said activity of the product is determined by reacting the reaction product with human lysine plasminogen or glutamyl plasminogen in the presence or absence of a tissue plasminogen activator simulator, acting the plasmin formed thereby on a chromogenic peptide substrate specific to the plasmin and measuring an amount of a substrate released from the chromogenic peptide substrate.

4. The method as claimed in claim 1, wherein said anti-tissue plasminogen activator antibody IgG fraction is an anti-t-PA monoclonal antibody SP-322 (Accession No. BP-3052), having specificity to t-PA, and which has the following properties:
   a) Molecular weight: $153,000 + 10,000$
   b) IgG subclass: IgG 1
   c) Amino acid sequence of variable region (L-chain):
      Asp-Ile-Val-Leu-Thr-Gln-Ser-Proc-Ala-Ser-Leu-Ala-Val-Ser
   d) Binding site against t-PA antigen: fibrin binding site.

5. The method as claimed in claim 2 wherein there is used as the anti-tissue plasminogen activator antibody IgG fraction, an anti-t-PA monoclonal antibody SP-322 (Accession No. FERM BP-3052), having specificity to t-PA and which has the following properties:
   a) Molecular weight: $153,000 + 10,000$
   b) IgG subclass: IgG 1
   c) Amino acid sequence of variable region (L-chain):
      Asp-Ile-Val-Leu-Thr-Gln-Ser-Pro-Ala-Ser-Leu-Ala-Val-Ser
   d) Binding site against t-PA antigen: fibrin binding site.

6. The method as claimed in claim 3 wherein there is used as the anti-tissue plasminogen activator antibody IgG fraction, an anti-t-PA monoclonal antibody SP-322 (Accession No. FERM BP-3052), having specificity to t-PA and which has the following properties:
   a) Molecular weight: $153,000 + 10,000$
   b) IgG subclass: IgG 1
   c) Amino acid sequence of variable region (L-chain):
      Asp-Ile-Val-Leu-Thr-Gln-Ser-Pro-Ala-Ser-Leu-Ala-Val-Ser
   d) Binding site against t-PA antigen: fibrin binding site.

* * * * *